United States Patent
Stevenson et al.

(10) Patent No.: US 8,246,606 B2
(45) Date of Patent: Aug. 21, 2012

(54) SYSTEMS AND METHODS FOR CONTROLLING INFLAMMATORY RESPONSE

(75) Inventors: Eric Stevenson, San Antonio, TX (US); Kenneth Norbury, San Antonio, TX (US); Richard Paul Mormino, San Antonio, TX (US); George Hutchinson, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 353 days.

(21) Appl. No.: 12/466,844

(22) Filed: May 15, 2009

(65) Prior Publication Data

US 2010/0069885 A1    Mar. 18, 2010

Related U.S. Application Data

(60) Provisional application No. 61/098,030, filed on Sep. 18, 2008.

(51) Int. Cl.
*A61M 1/00* (2006.01)

(52) U.S. Cl. ............................................. 604/540; 606/1

(58) Field of Classification Search .................... 604/19, 604/27, 28, 35, 93.01, 131, 245, 246, 264, 604/275, 540–543, 317, 327, 328, 355, 902; 156/292; 602/41–46, 48; 600/573, 575, 600/578; 424/447–449; 606/1
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |

(Continued)

FOREIGN PATENT DOCUMENTS

AU    550575 A1    8/1982

(Continued)

OTHER PUBLICATIONS

N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96 (certified translation).

(Continued)

*Primary Examiner* — Tatyana Zalukaeva
*Assistant Examiner* — Benedict L Hanrahan
(74) *Attorney, Agent, or Firm* — SNR Denton US, LLP

(57) ABSTRACT

A method and system for controlling inflammatory response at an internal tissue site of a patient utilizes a reduced-pressure treatment device. Controlling the inflammatory response may be accomplished in a number of ways that involve treating the inflammatory milieu. Treating the inflammatory milieu may include removing or moderating pro-inflammatory stimuli, e.g., fluids, enhancing perfusion of the tissue at or near the internal tissue site, or providing reduced-pressure therapy. The reduced-pressure treatment device is placed at or near the internal tissue site and is fluidly coupled to an external reduced-pressure source. The reduced-pressure treatment device provides reduced pressure proximate the tissue site and treats the inflammatory milieu. The reduced-pressure treatment device for controlling inflammatory response may be a minimally-invasive treatment device.

16 Claims, 8 Drawing Sheets

U.S. PATENT DOCUMENTS

| | | |
|---|---|---|
| 3,066,672 A | 12/1962 | Crosby, Jr. et al. |
| 3,367,332 A | 2/1968 | Groves |
| 3,520,300 A | 7/1970 | Flower, Jr. |
| 3,556,101 A | 1/1971 | Economou |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,830,238 A | 8/1974 | Kurtz et al. |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,294,240 A | 10/1981 | Thill |
| 4,297,995 A | 11/1981 | Golub |
| 4,333,468 A | 6/1982 | Geist |
| 4,346,711 A | 8/1982 | Agdanowski et al. |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,430,084 A | 2/1984 | Deaton |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,633,865 A | 1/1987 | Hengstberger et al. |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,728,642 A | 3/1988 | Pawelchak et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,815,468 A | 3/1989 | Annand |
| 4,825,866 A | 5/1989 | Pierce |
| 4,826,494 A | 5/1989 | Richmond et al. |
| 4,838,883 A | 6/1989 | Matsuura |
| 4,840,187 A | 6/1989 | Brazier |
| 4,844,072 A | 7/1989 | French et al. |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,899,965 A | 2/1990 | Usui |
| 4,906,233 A | 3/1990 | Moriuchi et al. |
| 4,906,240 A | 3/1990 | Reed et al. |
| 4,908,350 A | 3/1990 | Kramer et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,014,389 A | 5/1991 | Ogilvie et al. |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,192,266 A | 3/1993 | Wilk |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,437,683 A | 8/1995 | Neumann et al. |
| 5,441,481 A | 8/1995 | Mishra et al. |
| 5,443,848 A | 8/1995 | Kramer et al. |
| 5,466,231 A | 11/1995 | Cercone et al. |
| 5,484,399 A | 1/1996 | Diresta et al. |
| 5,484,428 A | 1/1996 | Drainville et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,637,103 A | 6/1997 | Kerwin et al. |
| 5,645,081 A | 7/1997 | Argenta et al. |
| 5,662,598 A | 9/1997 | Tobin |
| 5,701,917 A | 12/1997 | Khouri |
| 5,792,173 A | 8/1998 | Breen et al. |
| 5,893,368 A | 4/1999 | Sugerman |
| 5,902,260 A | 5/1999 | Gilman et al. |
| 5,938,626 A | 8/1999 | Sugerman |
| 6,042,539 A | 3/2000 | Harper et al. |
| 6,051,747 A | 4/2000 | Lindqvist et al. |
| 6,071,267 A | 6/2000 | Zamierowski |
| 6,135,116 A | 10/2000 | Vogel et al. |
| 6,174,306 B1 | 1/2001 | Fleischmann |
| 6,241,747 B1 | 6/2001 | Ruff |
| 6,264,979 B1 | 7/2001 | Svedman |
| 6,287,316 B1 | 9/2001 | Agarwal et al. |
| 6,345,623 B1 | 2/2002 | Heaton et al. |
| 6,383,162 B1 | 5/2002 | Sugarbaker |
| 6,458,109 B1 | 10/2002 | Henley et al. |
| 6,488,643 B1 | 12/2002 | Tumey et al. |
| 6,493,568 B1 | 12/2002 | Bell et al. |
| 6,537,241 B1 | 3/2003 | Odland |
| 6,553,998 B2 | 4/2003 | Heaton et al. |
| 6,626,891 B2 | 9/2003 | Ohmstede |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,814,079 B2 | 11/2004 | Heaton et al. |
| 6,855,135 B2 | 2/2005 | Lockwood et al. |
| 6,936,037 B2 | 8/2005 | Bubb et al. |
| 6,951,553 B2 * | 10/2005 | Bubb et al. .................. 604/327 |
| 6,979,324 B2 | 12/2005 | Byboard et al. |
| 7,105,001 B2 | 9/2006 | Mandelbaum |
| 7,128,735 B2 * | 10/2006 | Weston ........................ 604/543 |
| 7,195,624 B2 | 3/2007 | Lockwood et al. |
| 7,276,051 B1 | 10/2007 | Henley et al. |
| 7,284,730 B2 | 10/2007 | Walsh et al. |
| 7,322,971 B2 | 1/2008 | Shehada |
| 7,338,482 B2 | 3/2008 | Lockwood et al. |
| 7,381,859 B2 * | 6/2008 | Hunt et al. ...................... 602/46 |
| 7,476,205 B2 | 1/2009 | Erdmann |
| 7,790,945 B1 | 9/2010 | Watson, Jr. |
| 7,951,100 B2 | 5/2011 | Hunt et al. |
| 8,114,126 B2 | 2/2012 | Heaton et al. |
| 2002/0062097 A1 | 5/2002 | Simpson |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0115956 A1 | 8/2002 | Ross |
| 2002/0120185 A1 | 8/2002 | Johnson |
| 2002/0143286 A1 | 10/2002 | Tumey |
| 2002/0161317 A1 | 10/2002 | Risk et al. |
| 2003/0208149 A1 | 11/2003 | Coffey |

| | | | |
|---|---|---|---|
| 2004/0030304 A1 | 2/2004 | Hunt et al. | |
| 2005/0085795 A1 | 4/2005 | Lockwood | |
| 2005/0101922 A1 | 5/2005 | Anderson et al. | |
| 2005/0131327 A1 | 6/2005 | Lockwood et al. | |
| 2005/0222544 A1 | 10/2005 | Weston | |
| 2005/0261642 A1 | 11/2005 | Weston | |
| 2005/0273066 A1 | 12/2005 | Wittmann | |
| 2006/0029650 A1 | 2/2006 | Coffey | |
| 2006/0041247 A1 | 2/2006 | Petrosenko et al. | |
| 2006/0079852 A1 | 4/2006 | Bubb | |
| 2006/0189910 A1 | 8/2006 | Johnson et al. | |
| 2007/0185426 A1 | 8/2007 | Ambrosio et al. | |
| 2007/0282309 A1* | 12/2007 | Bengtson et al. | 604/541 |
| 2007/0293830 A1 | 12/2007 | Martin | |
| 2008/0058684 A1 | 3/2008 | Ugander et al. | |
| 2008/0103462 A1 | 5/2008 | Wenzel et al. | |
| 2008/0125687 A1 | 5/2008 | Flick et al. | |
| 2008/0167593 A1 | 7/2008 | Fleischmann | |
| 2008/0269658 A1 | 10/2008 | Vinton et al. | |
| 2009/0099519 A1 | 4/2009 | Kaplan | |
| 2010/0030132 A1 | 2/2010 | Niezgoda et al. | |

FOREIGN PATENT DOCUMENTS

| | | |
|---|---|---|
| AU | 745271 | 4/1999 |
| AU | 755496 | 2/2002 |
| CA | 2005436 | 6/1990 |
| CA | 2 303 085 | 3/1999 |
| DE | 26 40 413 A1 | 3/1978 |
| DE | 2754775 A1 | 6/1979 |
| DE | 43 06 478 A1 | 9/1994 |
| DE | 295 04 378 U1 | 10/1995 |
| DE | 20115990 U1 | 12/2001 |
| DE | 69806842 T2 | 1/2003 |
| DE | 60118546 T2 | 8/2006 |
| DE | 102006032870 | 1/2008 |
| EP | 0100148 A1 | 2/1984 |
| EP | 0117632 A2 | 9/1984 |
| EP | 0161865 A2 | 11/1985 |
| EP | 271491 B1 | 6/1988 |
| EP | 0358302 A2 | 3/1990 |
| EP | 0506992 | 10/1992 |
| EP | 0555293 | 8/1993 |
| EP | 0777504 | 6/1997 |
| EP | 0 853 950 B1 | 10/2002 |
| EP | 1284777 | 2/2003 |
| EP | 1 088 569 B1 | 8/2003 |
| EP | 1018967 B1 | 8/2004 |
| EP | 0 688 189 B2 | 6/2005 |
| EP | 0 620 720 B2 | 11/2006 |
| GB | 692578 | 6/1953 |
| GB | 2058227 A | 4/1981 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2342584 A | 4/2000 |
| GB | 2329 127 B | 8/2000 |
| GB | 2365350 | 2/2002 |
| JP | 3056429 U | 5/1991 |
| JP | 4129536 | 4/1992 |
| SG | 71559 | 4/2002 |
| WO | WO 80/02182 | 10/1980 |
| WO | WO 87/01027 A1 | 2/1987 |
| WO | WO 87/04626 | 8/1987 |
| WO | WO 90/10424 | 9/1990 |
| WO | WO 92/07519 A1 | 5/1992 |
| WO | WO 93/09727 | 5/1993 |
| WO | WO 94/20041 | 9/1994 |
| WO | WO 96/05873 | 2/1996 |
| WO | WO 96/34636 A | 11/1996 |
| WO | WO 97/18007 | 5/1997 |
| WO | WO 99/01173 A1 | 1/1999 |
| WO | WO 99/13793 | 3/1999 |
| WO | WO 00/07653 A1 | 2/2000 |
| WO | WO 00/42958 A1 | 7/2000 |
| WO | WO 00/57794 A1 | 10/2000 |
| WO | WO 00/59418 A1 | 10/2000 |
| WO | WO 00/59424 A1 | 10/2000 |
| WO | WO 01/34223 A1 | 5/2001 |
| WO | WO 01/71231 A1 | 9/2001 |
| WO | WO 01/85248 A | 11/2001 |
| WO | WO 01/89431 A1 | 11/2001 |
| WO | WO 03/057307 A1 | 7/2003 |
| WO | WO 03/086232 | 10/2003 |
| WO | WO 2006/048246 A1 | 5/2006 |
| WO | WO 2006/114637 A2 | 11/2006 |
| WO | WO 2007/031762 A | 3/2007 |
| WO | WO 2007/041642 A | 4/2007 |
| WO | WO 2007/109209 A2 | 9/2007 |
| WO | WO 2007/133618 A2 | 11/2007 |
| WO | WO 2008/014358 A2 | 1/2008 |
| WO | WO 2008/040020 A | 4/2008 |
| WO | WO 2008/041926 A1 | 4/2008 |
| WO | WO 2008/103625 A2 | 8/2008 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Ðukić, Ž. Maksimović, Ð. Radak, and P. Peška, "Vacuum Therapy in the Treatment of Peripheral Blood Vessels," *Timok Medical Journal* 11 (1986), pp. 161-164 (certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax,"*Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, Pa 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
Restriction Requirement dated Jan. 4, 2010 in U.S. Appl. No. 12/466,973.
Response filed Jan. 21, 2010 to Restriction Requirement dated Jan. 4, 2010 in U.S. Appl. No. 12/466,973.
Non-Final Action date mailed Mar. 5, 2010 in U.S. Appl. No. 12/466,973.
The V.A.C. TM Vacuum Assisted Closure, Assisting in Wound Closure, Brochure, Jan. 1996, 5 pages, 1-A-042, KCI®, San Antonio, Texas.
Argenta et al: "The V.A.C. TM, Case Study #4", Case Study, Mar. 1995, 1 page, 35-D-004, KCI®, San Antonio, Texas.
Argenta et al: "The V.A.C. TM, Case Study #3", Case Study, Mar. 1995, 1 page, 35-D-003, KCI®, San Antonio, Texas.
"The V.A.C.® Operations Summary, The V.A.C.® Wound Closure System Applcations", Brochure, Mar. 1999, 2 pages, 1-A-060, KCI®, San Antonio, Texas.
Argenta et al.: "V.AC.® Wound Closure Device Case Study #3", Case Study, Apr. 1998, 1 page, 35-D-003, KCI®, San Antonio, Texas.
"The V.A.C.® Operations Summary, The V.A.C.® Wound Closure System Applcations", Brochure, Mar. 1997, 4 pages, 1-A-060, KCI®, San Antonio, Texas.
Argenta et al.: "V.AC.® Wound Closure Device Case Study #1", Case Study, Apr. 1998, 1 page, 35-D-001, KCI®, San Antonio, Texas.
The V.A.C.® Case Study #8, Case Study, Jun. 1996, 2 pages, 35-D-008, KCI®, San Antonio, Texas.
The V.A.C.® Case Study #7, Case Study, Jun. 1996, 2 pages, 35-D-007, KCI®, San Antonio, Texas.
The V.A.C.® Case Study #6, Case Study, Jun. 1996, 2 pages, 35-D-006, KCI®, San Antonio, Texas.
The V.A.C.® Case Study #9, Case Study, Jun. 1996, 2 pages, 35-D-009, KCI®, San Antonio, Texas.
The V.A.C.® Case Study #5, Case Study, Aug. 1994, 2 pages, 35-D-005, KCI®, San Antonio, Texas.
The V.A.C.® Case Study #4, Case Study, Aug. 1994, 2 pages, 35-D-004, KCI®, San Antonio, Texas.
The V.A.C.® Case Study #3, Case Study, Aug. 1994, 2 pages, 35-D-003, KCI®, San Antonio, Texas.
The V.A.C.® Case Study #2, Case Study, Aug. 1994, 2 pages, 35-D-002, KCI®, San Antonio, Texas.
The V.A.C.® Case Study #1, Case Study, Aug. 1994, 2 pages, 35-D-001, KCI®, San Antonio, Texas.
Ex parte Quayle Office Action dated Feb. 7, 2005 for U.S. Appl. No. 10/275,671.
Amendment filed Apr. 8, 2005 for U.S. Appl. No. 10/275,671.
Non-Final Office Action dated Jun. 27, 2005 for U.S. Appl. No. 10/275,671.
Response filed Oct. 19, 2005 for U.S. Appl. No. 10/275,671.
Non-Final Office Action dated Jan. 10, 2006 for U.S. Appl. No. 10/275,671.
Response filed Jul. 10, 2006 for U.S. Appl. No. 10/275,671.
Supplemental Amendment filed Aug. 10, 2006 for U.S. Appl. No. 10/275,671.
Final Office Action dated Apr. 17, 2007 for U.S. Appl. No. 10/275,671.
Response filed Jun. 12, 2007 for U.S. Appl. No. 10/275,671.
Advisory Action dated Jul. 11, 2007 for U.S. Appl. No. 10/275,671.
Response filed Aug. 17, 2007 for U.S. Appl. No. 10/275,671.
Non-Final Office Action dated Sep. 5, 2007 for U.S. Appl. No. 10/275,671.
Response filed Sep. 5, 2007 for U.S. Appl. No. 10/275,671.
Notice of Allowance and Fee(s) Due dated Feb. 4, 2008 for U.S. Appl. No. 10/275,671.
Restriction Requirement date mailed Nov. 10, 2009 for U.S. Appl. No. 12/127,668.
Response filed Dec. 10, 2009 for U.S. Appl. No. 12/127,668.
Office Action date mailed Mar. 23, 2010 for U.S. Appl. No. 12/127,668.
Response filed Jun. 23, 2010 for U.S. Appl. No. 12/127,668.
Interview Summary date mailed May 25, 2010 for U.S. Appl. No. 12/466,973.
Final Office Action date mailed Aug. 12, 2010 for U.S. Appl. No. 12/466,973.
Smith & Nephew GmbH Nullity Action date mailed Sep. 10, 2010.
Response filed Oct. 4, 2010 for U.S. Appl. No. 12/466,973.
Advisory Action date mailed Oct. 12, 2010 for U.S. Appl. No. 12/466,973.
RCE/Response filed Nov. 2, 2010 for U.S. Appl. No. 12/466,973.
Response filed May 20, 2010 to Non-Final Action date mailed Mar. 5, 2010 in U.S. Appl. No. 12/466,973.
Meyer et al, "A new abdominal drain for overflowing lavage in instances of severe pancreatitis with persistent peritoneal contamination", Surg. Gynecol Obstet. Sep. 1987: 165(3): 271-3.
Poritz, "Percutaneous drainage and ileocolectomy for spontaneous intraabdominal abscess in Chrohns Disease" J. Gastrointest Surg. Feb. 2007; 11(2): 204-8.

Khurrum et al, "Percutaneous postoperative intra-abdominal abscess drainage after elective colorectal surgery" Tech Coloprotoci Dec. 2002: 6(3): 159-64.

Reckard et al, "Management of Intraabdominal Hypertension by Percutaneous Catheter Drainage" Journal of Vascual Interventional Journal of Vascual Interventional Radiology, vol. 16, Issue 7, pp. 1019-1021.

Latenser et al, "A Pilot Study Comparing Percutaneous Decompression with decompressive laparotomy for acute abdominal compartment syndrome in thermal injury", J Burn Care & Rehav, 23(3): 190-195.

Kubiak et al, "Reduced intra-peritoneal inflammation by negative pressure therapy moderates systemic inflammation in a porcine modiel of the abdominal compartment Syndrome (ACS)", Critical Care I, vol. 207, No. 3S, Sep. 2008, S34-35.

Kaplan, "Managing the open abdomen" Ostomy Wound Management, Jan. 2004; 50 1A supply; C2; 1-8.

Kaplan et al, "Guidelines for the Management of the Open Abdomen" Wounds Oct. 2005; 17 (Suppl 1) ; S1S24.

Garner et al, "Vacuum-assisted wound closure provides early fascial reapproximation in trauma patients with open abdomens" The American Journal of Surgery, Dec. 2001; 182 (6) ; 630-8.

Barker et al, "Vacuum pack of technique of temporary abdominal closure; a 7-year experience with 112 patients" J Trauma Feb. 1, 2000; 48 (2): 201-6.

Brock et a;, "Temporary closure of open abdominal wounds: the vacuum pack" Am Surg Jan. 1995; 61(1): 30-5.

Sherck et al, "Covering the 'open abdomen': a better technique", Am Surg Sep. 1998; 64(9): 854-7.

Dubick et al, "Issues of concern regarding the use of hypertonic/hyperoncotic fluid resuscitation of hemorrhagic hypotension" Shock, Apr. 2006; 25(4): 321-8.

Burdette:, "Systemic Inflammatory Response Syndrome", http://emedicine.medscape.com/article/168943-print, Apr. 2007.

Beamis Hyrdorphobic Rigid Canisters—http://www.bemishealthcare.com/docs/CanisterHydrophobic.pdf (date unknown).

Fink et al, "Textbook of Critical Care", $5^{th}$ ed. (Philadelphia: Elsevier, 2005), 1933-1943.

Kubiak et al, "Peritoneal Negative Pressure Therapy Prevents Multiple Organ Injury in a Chronic Porcine Sepsis and lschemia/Reperfusion Model", Shock, vol. 34, No. 5, pp. 525-534, 2010.

Response filed Nov. 9, 2010 for U.S. Appl. No. 12/127,668.

Notice of Allowance date mailed Dec. 6, 2010 for U.S. Appl. No. 12/127,668.

Final Office Action date mailed Sep. 16, 2010 for U.S. Appl. No. 12/127,668.

International Search Report and Written Opinion date mailed Nov. 5, 2009; PCT International Application No. PCT/US2009/044264.

International Search Report and Written Opinion date mailed Nov. 18, 2009; PCT International Application No. PCT/US2009/044230.

International Search Report and Written Opinion date mailed Sep. 17, 2009; PCT International Application No. PCT/US2009/044240.

International Search Report and Written Opinion date mailed Nov. 5, 2009; PCT International Application No. PCT/US2009/044268.

International Search Report and Written Opinion date mailed Oct. 6, 2009; PCT International Application No. PCT/US2009/044226.

International Search Report and Written Opinion date mailed Oct. 15, 2009; PCT International Application No. PCT/US2009/044244.

International Search Report and Written Opinion date mailed Oct. 6, 2009; PCT International Application No. PCT/US2009/044266.

International Search Report and Written Opinion date mailed Nov. 5, 2009; PCT International Application No. PCT/US2009/044245.

International Search Report and Written Opinion date mailed Oct. 23, 2009; PCT International Application No. PCT/US2009/044235.

Non-Final Office Action date mailed Sep. 8, 2011 for U.S. Appl No. 12/467,203.

Response filed Nov. 15, 2011 for U.S. Appl. No. 12/467,203.

Interview Summa date mailed Nov. 17, 2011 for U.S. Appl. No. 12/467,203.

Notice of Allowance date mailed Dec. 2, 2011 for U.S. Appl. No. 12/467,203.

Response filed Nov. 15, 2011 for U.S. Appl. No. 12/467,064.

Response filed Sep. 9, 2011 for U.S. Appl. No. 12/467,211.

Non-Final office Action date mailed Nov. 21, 2011 for U.S. Appl. No. 12/467,211.

Non-Final Office Action date mailed Nov. 4, 2011 for U.S. Appl. No. 12/467,123.

Non-Final Office Action date mailed Sep. 20, 2011 for U.S. Appl. No. 12/467,168.

Response filed Nov. 18, 2011 for U.S. Appl. No. 12/467,168.

Interview Summary date mailed Nov. 25, 2011 for U.S. Appl. No. 12/467,168.

Notice of Allowance date mailed Nov. 4, 2011 for U.S. Appl. No. 12/467,199.

Non-Final Office Action date mailed Sep. 14, 2011 for U.S. Appl. No. 13/113,914.

Response filed Dec. 14, 2011 for U.S. Appl. No. 13/113,914.

Interview Summary date mailed Jan. 6, 2012 for U.S. Appl. No. 12/467,123.

Response filed Jan. 9, 2012 for U.S. Appl. No. 12/467,123.

Interview Summary date mailed Dec. 21, 2011 for U.S. Appl. No. 13/113,914.

Non-Final Office Action and Interview Summary date mailed Sep. 6, 2011 for U.S. Appl. No. 12/467,064.

Restriction Requirement date mailed Aug. 12, 2011 for U.S. Appl. No. 12/467,211 11.

Restriction Requirement date mailed Jul. 21, 2011 for U.S. Appl. No. 12/467,123.

Response filed for U.S. Appl. No. 12/467,123.

Restriction Requirement date mailed Aug. 4, 2011 for U.S. Appl. No. 12/467,153.

Response filed for U.S. Appl. No. 12/467,153.

Restriction Requirement date mailed Jul. 27, 2011 for U.S. Appl. No. 12/467,199.

Response filed for U.S. Appl. No. 12/467,199.

Notice of Allowance date mailed Feb. 9, 2012 for U.S. Appl. No. 12/467,064.

Response filed Feb. 8, 2012 for U.S. Appl. No. 12/467,211.

Notice of Allowance date mailed Mar. 1, 2012 for U.S. Appl. No. 12/467,168.

Notice of Allowance date mailed Feb. 24, 2012 for U.S. Appl. No. 13/113,914.

Notice of Allowance date mailed Jan. 31, 2012 for U.S. Application No. 12/467,153.

US 6,216,701, 04/2001, Heaton (withdrawn)

* cited by examiner

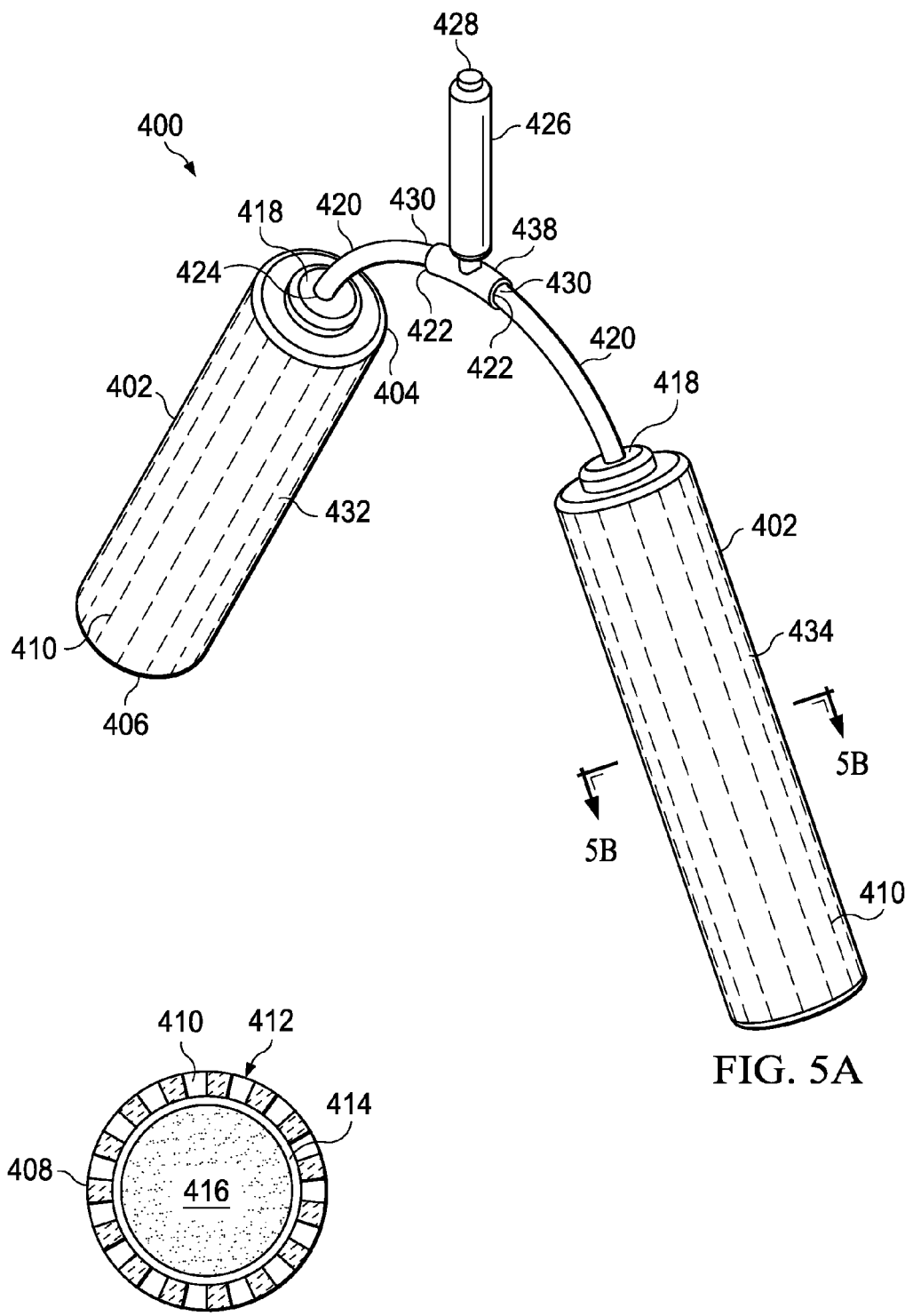

SYSTEMS AND METHODS FOR CONTROLLING INFLAMMATORY RESPONSE

RELATED APPLICATIONS

The present invention claims the benefit, under 35 USC §119(e), of the filing of U.S. Provisional Patent Application Ser. No. 61/098,030, entitled "Fluid Removal System and Method," filed Sep. 18, 2008, which is incorporated herein by reference for all purposes.

BACKGROUND

The present invention relates generally to medical treatment systems and, more particularly, to systems and methods for controlling inflammatory response in a patient.

One type of inflammatory response is systemic inflammatory response syndrome (SIRS). SIRS has been defined as a severe systemic response to a condition (trauma, infection, burn, etc.) that provokes an acute inflammatory reaction indicated by the presence of two or more of a group of symptoms including abnormally increased or decreased body temperature, heart rate greater than 90 beats per minute, respiratory rate greater than 20 breaths per minute or a reduced concentration of carbon dioxide in the arterial blood, and the white blood cell count greatly decreased or increased or consisting of more than ten percent immature neutrophils. *Merriam-Webster's Medical Dictionary* (Springfield, Mo.: Merriam-Webster, Inc., 2006), q.v., "Systemic inflammatory response syndrome." SIRS is nonspecific and can be caused by ischemia, inflammation, trauma, infection, or a combination of several insults. Sepsis is a subcategory of SIRS that may be defined as the presence of SIRS in addition to a documented or presumed infection.

Irrespective of etiology, SIRS typically has the same pathophysiologic properties, with minor differences, in inciting inflammation or inflammatory cascade. The inflammatory cascade is a complex process that may involve humoral and cellular responses, complement, and cytokine cascades. It is believed that pro-inflammatory stimuli can interact directly with tissue to promote SIRS. Unchecked SIRS may lead to abdominal compartment syndrome (ACS), organ dysfunction, multiple organ dysfunction syndrome (MODS), multiple organ failure (MOF), and death.

In many instances, if SIRS is severe enough, intervention becomes necessary. For example, if SIRS leads or begins to lead to ACS, surgical decompression may be utilized. Surgical decompression involves a laparotomy in which a surgeon forms an anterior, midline incision from the patient's sternum to near the pubic bone. The abdominal contents are then freed to expand beyond the abdominal cavity. This type of intervention is costly given the long hospital stay associated with such a procedure, the increased morbidity and mortality, and as a result the decision to intervene with a laparotomy is often delayed as long as possible because of the severity of the intervention.

It is desirable to control SIRS and other types of inflammatory response. Moreover, it is generally desirable to control inflammatory response as soon as possible and as cost effectively as possible.

SUMMARY

Problems with medical treatment systems and methods are addressed by the systems and methods of the illustrative embodiments described herein. According to one illustrative embodiment, a method for controlling systemic inflammatory response in a patient's abdominal cavity includes the steps of deploying a treatment device into the patient's abdominal cavity; fluidly coupling an external reduced-pressure source to the treatment device to provide reduced pressure within the abdominal cavity; providing reduced pressure from the external reduced-pressure source to the treatment device; and removing pro-inflammatory stimuli from the abdominal cavity to control systemic inflammatory response.

According to another illustrative embodiment, a system for controlling systemic inflammatory response in a patient's abdominal cavity includes a treatment device for deploying into the patient's abdominal cavity. The treatment device may be a minimally-invasive treatment device. The system for controlling systemic inflammatory response in a patient's abdominal cavity further includes a sealing member for disposing on a portion of a patient's epidermis and operable to form a pneumatic seal over the abdominal cavity; an external reduced-pressure source for supplying reduced pressure; and a reduced-pressure delivery conduit for fluidly coupling the reduced-pressure source and the connecting interface. The reduced-pressure source, reduced-pressure delivery conduit, and treatment device are operable to provide reduced pressure from the external reduced-pressure source to the treatment device, and to remove pro-inflammatory stimuli fluids from the abdominal cavity.

According to another illustrative embodiment, a method for controlling systemic inflammatory response in a patient's abdominal cavity includes the steps of: deploying a reduced-pressure treatment device into the patient's abdominal cavity and fluidly coupling an external reduced-pressure source to the reduced-pressure treatment device to provide reduced pressure within the abdominal cavity. The method for controlling systemic inflammatory response further includes providing reduced pressure from the external reduced-pressure source to the reduced-pressure treatment device; and removing pro-inflammatory stimuli fluids from the abdominal cavity and providing reduced-pressure therapy in the abdominal cavity to control systemic inflammatory response.

Other objects, features, and advantages of the illustrative embodiments will become apparent with reference to the drawings and detailed description that follow.

BRIEF DESCRIPTION OF THE DRAWINGS

FIG. 5A is a schematic, perspective view of an illustrative embodiment of a reduced-pressure treatment device; and FIG. 5B is a schematic, cross sectional view of the illustrative embodiment of a reduced-pressure treatment device of FIG. 5A taken along plane 5B-5B.

DETAILED DESCRIPTION OF ILLUSTRATIVE EMBODIMENTS

Figure 1A:
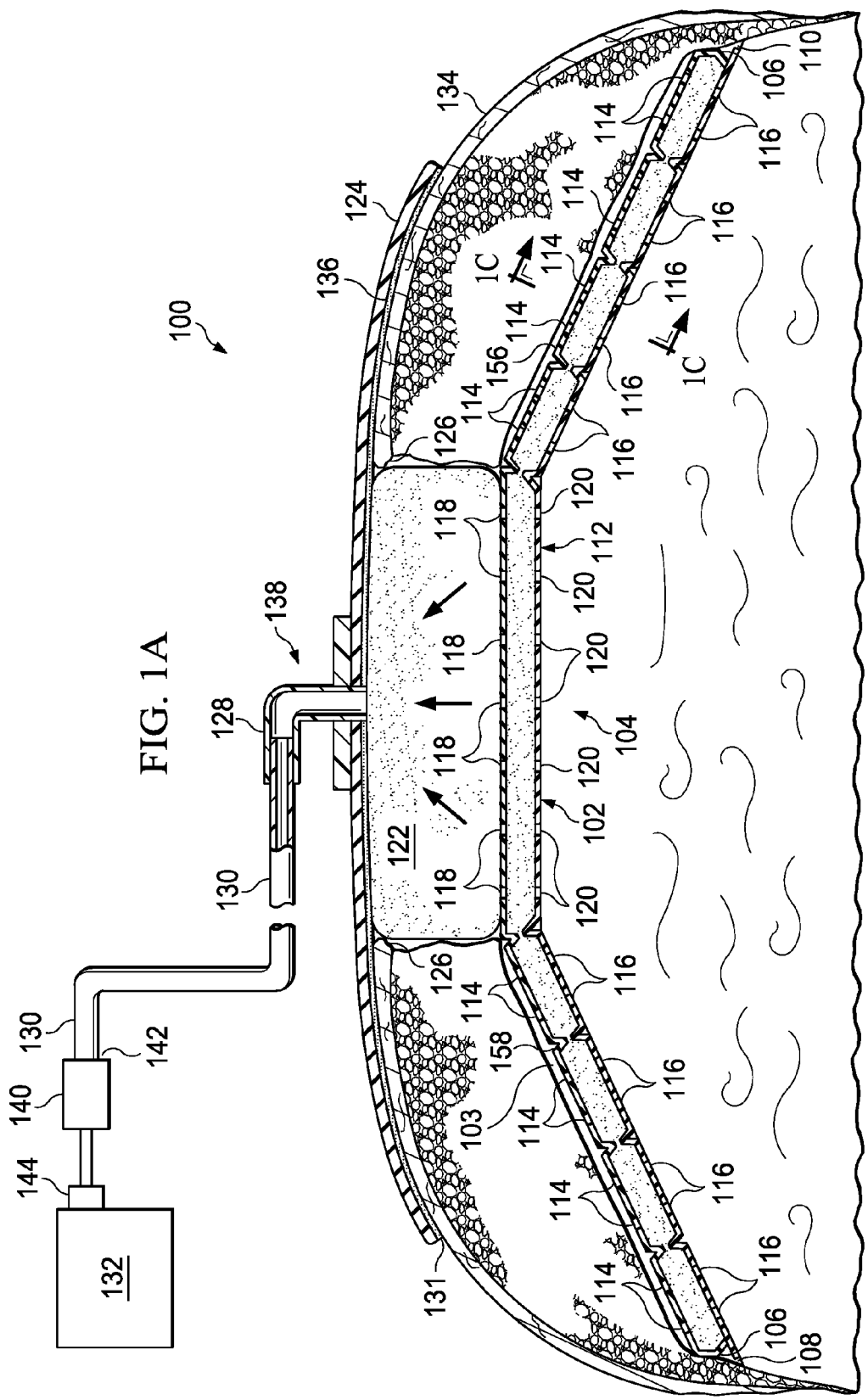
FIG. 1A is a schematic, cross sectional view, with a portion shown as a block diagram, of an illustrative embodiment of a system for controlling systemic inflammatory response in a patient's abdominal cavity.
Figure 1B:
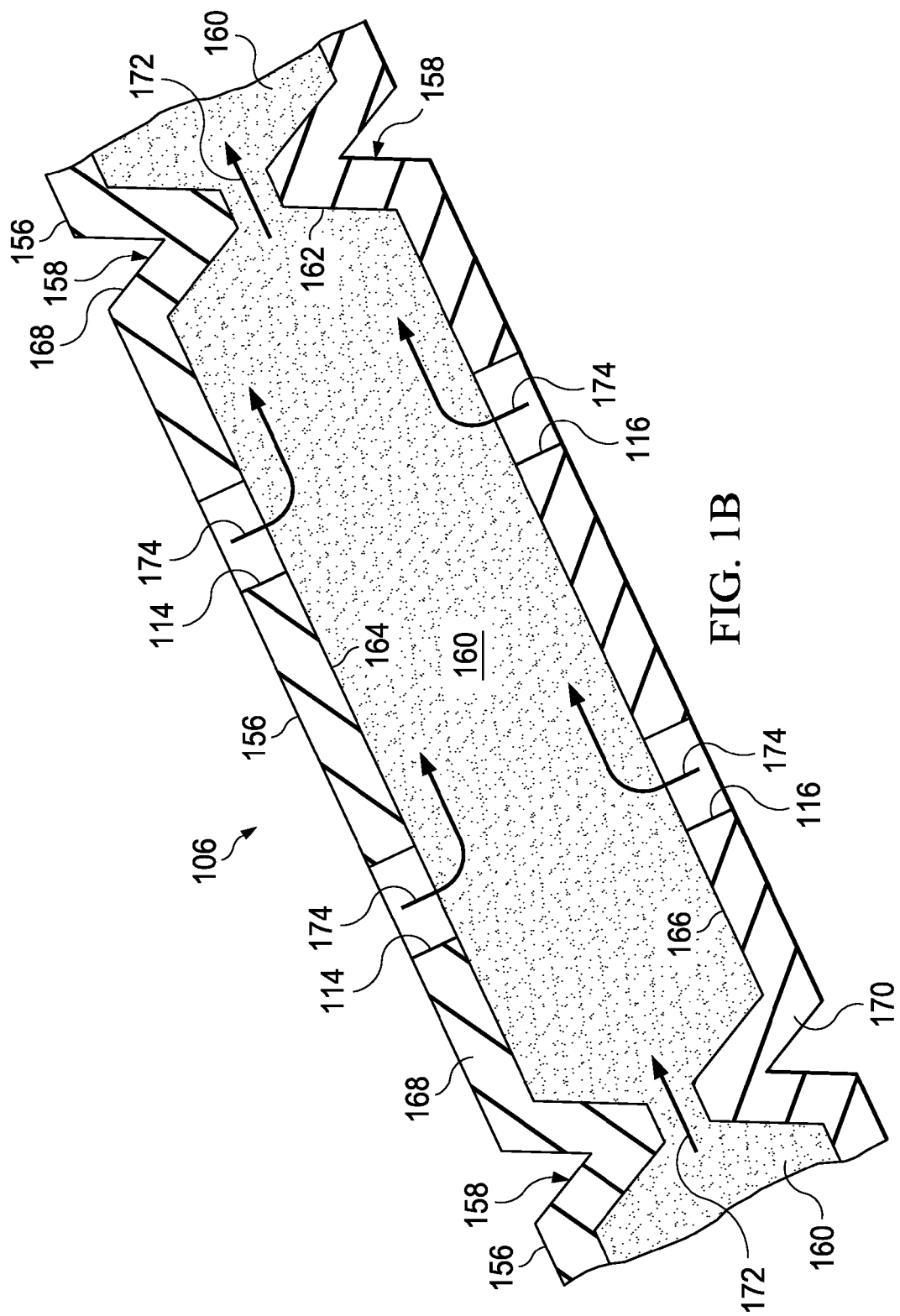
FIG. 1B is a detail of an encapsulated leg member of the system for controlling systemic inflammatory response in a patient's abdominal cavity of FIG. 1A.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Illustrative systems and devices herein allow for the control of inflammatory response including systemic inflammatory response and local inflammatory response at an internal tissue site. "Control of inflammatory response" as used herein includes preventing or moderating the inflammatory response. Controlling the inflammatory response may be accomplished in a number of ways that involve treating the inflammatory milieu. Treating the inflammatory milieu may include removing or moderating pro-inflammatory stimuli, e.g., fluids, enhancing perfusion of the tissue at or near the internal tissue site, or providing reduced-pressure therapy. Unless otherwise indicated, as used herein, "or" does not require mutual exclusivity. As a more specific, illustrative example, controlling the inflammatory response may be accomplished by removing cytokines, chemokines, and other stimulants from proximate the internal tissue site. This approach involves increasing the rate of clearance. As another more specific, illustrative example, controlling the inflammatory response may be accomplished by improving the health of the local tissue, such as by increased perfusion, to decrease pro-inflammatory signaling thereby cutting off the source of the cascade and preventing a physiological response. This approach involves decreasing the rate of appearance. As another more specific, illustrative example, controlling the inflammatory response may be accomplished by increasing the production of anti-inflammatory signals and cytokines to act as agonists or antagonists or generally to block receptor sites for pro-inflammatory cytokines. This example will help to restore homeostasis and blunt the inflammatory physiologic responses and involves neutralizing the response.

The illustrative systems and devices may be used to treat an internal tissue site that may be the bodily tissue of any human, animal, or other organism. The internal tissue site may be a tissue space, e.g., a body cavity, such as an abdominal cavity. The internal tissue site may also be located in other tissue spaces such as a patient's arm, leg, skull, or other site. With respect to the tissue space, a number of approaches to deploying and removing the illustrative systems and devices may be used. For example, the illustrative systems and devices may be (1) deployed and removed through an open wound, see, e.g., FIG. 1; (2) deployed through an open wound and removed through one or more device incisions, see, e.g., FIGS. 3A-5B; or (3) deployed and removed through one or more device incisions, see, e.g., FIGS. 3A-5B.

Referring now to FIGS. 1A-1D, an illustrative embodiment of a system 100 for controlling inflammatory response, e.g., systemic inflammatory response, at an internal tissue site 104, such as in a patient's abdominal cavity 103, is presented. The system 100 includes a treatment device 102. The system 100 for controlling inflammatory response in a patient's abdominal cavity 103 delivers a treatment that controls inflammatory response, including systemic inflammatory response syndrome, and may help avoid abdominal compartment syndrome. While inflammatory response may occur without a rise in intra-abdominal pressure, in one particular, non-limiting example, controlling inflammatory response may involve avoiding a pressure rise in the abdominal cavity 103 altogether or at least maintaining the intra-abdominal pressure below 15 mm Hg and preferably below 13 mm Hg and even more preferably below 10 mm Hg. Normal intra-abdominal pressure is said to be in the range of about 0-5 mm Hg. The intra-abdominal pressure may be monitored by directly inserting a catheter into the abdominal compartment or indirectly by monitoring pressure in the bladder, stomach, or other cavities.

The system 100 controls the inflammation by treating an inflammatory milieu associated with the internal tissue site 104 of a patient. Treating the inflammatory milieu may include the approaches previously mentioned, including removing pro-inflammatory stimuli, enhancing perfusion of the tissue at or near the internal tissue site 104, or providing reduced-pressure therapy. In one embodiment, the system 100 is operable to remove substantially all the inflammatory stimuli, which may include removing the majority of the fluids in the abdominal cavity 103 so as to disrupt the inflammatory environment or improve local tissue health. In another illustrative embodiment, the system 100 is operable to moderate the inflammatory stimuli to disrupt the inflammatory environment or improve local tissue health. Using the treatment device 102 deployed in the abdominal cavity 103 to provide treatment may reduce the level of inflammatory stimuli, or mediators, such as interluekin-6 (IL-6) and TNF-α as measured in a peritoneal catheter fluid. The treatment device 102 may be used with a system and method to remove fluids that are pro-inflammatory stimuli from proximate the internal tissue site 104 over a time duration (T). The time that the treatment may be conducted may range from half an hour to 50 hours or more. By treating the inflammatory milieu, e.g., moderating the pro-inflammatory stimuli, the onset of an inflammatory response is controlled, e.g., avoided or delayed, and the severity may be reduced.

The treatment device 102 provides for the removal of abdominal fluids or pro-inflammatory stimuli with great reliability. The system 100 does not typically clog or otherwise have effectiveness diminish with use. The reduced-pressure therapy provided by the treatment device 102 may provide better perfusion of tissue within the abdominal cavity 103 and this may account for an additional measure of control of the inflammatory response. The treatment device 102 helps, among other things, to manage fluids, reduce edema, and reduces the risk of developing multiple organ dysfunction (MODS) secondary to inflammatory response. The treatment device 102 may be used in applications within the abdominal cavity 103 and to treat bowel edema. The treatment device 102 may also be used when a partial laparotomy is performed.

The internal tissue site 104 treated may be the bodily tissue of any human, animal, or other organism. In this illustrative embodiment, the internal tissue site 104 includes tissue in a body cavity, and in particular the abdominal cavity 103, and includes the abdominal contents or tissue that is proximate the abdominal cavity. In other illustrative applications, the internal tissue site may be located in a tissue space, or compartment, of a patient's arm, leg, skull, or other site.

As shown, the treatment device 102 is disposed within the abdominal cavity 103 of the patient to help control the inflammatory response-local or systemic. In this embodiment, the treatment device 102 is for deployment and removal through an open abdomen. The treatment device 102 includes a plurality of encapsulated leg members 106 that are supported by the abdominal contents, which make up a surface on which the plurality of encapsulated leg members 106 are placed. One or more of the plurality of encapsulated leg members 106 may be placed in or proximate to a first paracolic gutter 108, and one or more of the plurality of encapsulated leg members 106 may be placed in or proximate to a second paracolic gutter 110. The plurality of encapsulated leg members 106 is coupled to a central connection member 112, and there is fluid communication between the plurality of encapsulated leg members 106 and the central connection member 112. Both the plurality of encapsulated leg members 106 and the central connection member 112 may be formed with fenestrations 114, 116, 118, 120 that allow fluids in the abdominal cavity 103 to pass through. The fenestrations 114, 116, 118, 120 may take any shape, e.g., circular apertures, rectangular openings, polygons, etc., but are presented in this illustrative embodiment as slits, or linear cuts. One or more fenestrations 114, 116, 118, 120 might be omitted in alternative embodiments.

A manifold 122, or manifold pad, distributes reduced pressure to the treatment device 102. Alternatively, a connecting interface (e.g., connecting interface 220 in FIG. 3A) may be coupled to the treatment device 102 to supply reduced pressure (and remove fluids). A sealing member 124 provides a pneumatic seal over the abdominal cavity 103 or a body-cavity opening 126. One or more skin closure devices may be placed on a patient's epidermis 134 or abdominal wall (not shown). Reduced pressure is delivered to the manifold 122 through a reduced-pressure interface 128, which is coupled to a reduced-pressure delivery conduit 130. An external reduced-pressure source 132 delivers reduced pressure to the reduced-pressure delivery conduit 130. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling means that fluid is in communication between the designated parts or locations.

Reduced pressure may be applied to the internal tissue site 104 to help promote removal of pro-inflammatory stimuli, which may include ascites, cytokines, exudates, blood (in the case of trauma), or other fluids from the internal tissue site 104. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures.

The manifold 122 is positioned proximate the central connection member 112. The manifold 122 may take many forms. The term "manifold" as used herein generally refers to a substance or structure that is provided to assist in applying reduced pressure to, delivering fluids to, or removing fluids from the internal tissue site 104. The manifold 122 typically includes a plurality of flow channels or pathways that are interconnected to improve distribution of fluids provided to and removed from the internal tissue site 104 around the manifold 122 and through the central connection member 112. The manifold 122 may be a biocompatible material that is capable of being placed in contact with the internal tissue site 104 and distributing reduced pressure to the internal tissue site 104. Examples of the manifold 122 may include, without limitation, devices that have structural elements arranged to form flow channels, cellular foam, such as open-cell foam, porous tissue collections, liquids, gels and foams that include or cure to include flow channels. The manifold 122 may be porous and may be made from foam, gauze, felted mat, or any other material suited to a particular biological application. In one embodiment, the manifold 122 is a porous foam and includes a plurality of interconnected cells or pores that act as flow channels. The porous foam may be a polyurethane, open-cell, reticulated foam, such as a GranuFoam® material manufactured by Kinetic Concepts, Incorporated of San Antonio, Tex. Other embodiments might include "closed cells." In some situations, the manifold 122 may also be used to distribute fluids, such as medications, antibacterials, growth factors, and various solutions to the internal tissue site 104. Other layers may be included in or on the manifold 122, such as absorptive materials, wicking materials, hydrophobic materials, and hydrophilic materials.

The sealing member 124 is placed over the body-cavity opening 126, e.g., abdominal cavity 103, and provides a pneumatic seal adequate for the open-cavity, reduced-pressure system 100 to hold reduced pressure at the internal tissue site 104. The sealing member 124 may be a cover that is used to secure the manifold 122 on the central connection member 112. The sealing member 124 may be impermeable or semi-permeable. The sealing member 124 is capable of maintaining reduced pressure at the internal tissue site 104 after installation of the sealing member 124 over the body-cavity opening 126. The sealing member 124 may be a flexible over-drape or film formed from a silicone-based compound, acrylic, hydrogel or hydrogel-forming material, or any other biocompatible material that includes the impermeability or permeability characteristics as desired for applying reduced pressure to the internal tissue site 104.

The sealing member 124 may further include an attachment device 131 to secure the sealing member 124 to the patient's epidermis 134. The attachment device 131 may take many forms; for example, an adhesive layer 136 may be positioned along a perimeter of the sealing member 124 or any portion of the sealing member 124 to provide, directly or indirectly, the pneumatic seal with the patient's epidermis 134. The adhesive layer 136 might also be pre-applied to the sealing member 124 and covered with a releasable backing, or member (not shown), that is removed at the time of application.

The reduced-pressure interface 128 may be, as one example, a port or connector 138, which permits the passage of fluid from the manifold 122 to the reduced-pressure delivery conduit 130 and vice versa. For example, fluid collected from the internal tissue site 104 using the manifold 122 and the treatment device 102 may enter the reduced-pressure delivery conduit 130 via the connector 138. In another embodiment, the open-cavity, reduced-pressure system 100 may omit the connector 138 and the reduced-pressure delivery conduit 130 may be inserted directly into the sealing member 124 and into the manifold 122. The reduced-pressure delivery conduit 130 may be a medical conduit or tubing or any other means for transporting a reduced pressure and fluid.

The reduced-pressure delivery conduit 130 may be a multi-lumen member for readily delivering reduced pressure and removing fluids. In one embodiment, the reduced-pressure delivery conduit 130 is a two-lumen conduit with one lumen for reduced pressure and liquid transport and one lumen for communicating pressure to a pressure sensor.

Reduced pressure is supplied to the reduced-pressure delivery conduit 130 by the external reduced-pressure source 132. A wide range of reduced pressures may be generated or supplied by the external reduced-pressure source 132. In one embodiment, the range may include the range −50 to −300 mm Hg and in another embodiment, the range may include −100 mm Hg to −200 mm Hg. In one illustrative embodiment, the external reduced-pressure source 132 includes preset selectors for −100 mm Hg, −125 mm Hg, and −150 mm Hg. The external reduced-pressure source 132 may also include a number of alarms, such as a blockage alarm, a leakage alarm, or a battery-low alarm. The external reduced-pressure source 132 may be a portable source, wall source, or other unit for abdominal cavities. The external reduced-pressure source 132 may selectively deliver a constant pressure, intermittent pressure, or pressure with a dynamic or set pattern. The fluid removed from the cavity through the reduced-pressure delivery conduit 130 could be as much as 5 L or more per day.

A number of different devices, e.g., a representative device 140, may be added to a medial portion 142 of the reduced-pressure delivery conduit 130. For example, the representative device 140 might be a fluid reservoir, or canister collection member, a pressure-feedback device, a volume detection system, a blood detection system, an infection detection system, a filter, a port with a filter, a flow monitoring system, a temperature monitoring system, etc. Multiple representative devices 140 might be included. Some of these devices, e.g., the fluid collection member, may be formed integral to the external reduced-pressure source 132. For example, a reduced-pressure port 144 on the external reduced-pressure source 132 may include a filter member (not shown) that includes one or more filters and may include a hydrophobic filter that prevents liquid from entering an interior space of the external reduced-pressure source 132.

Figure 1C:
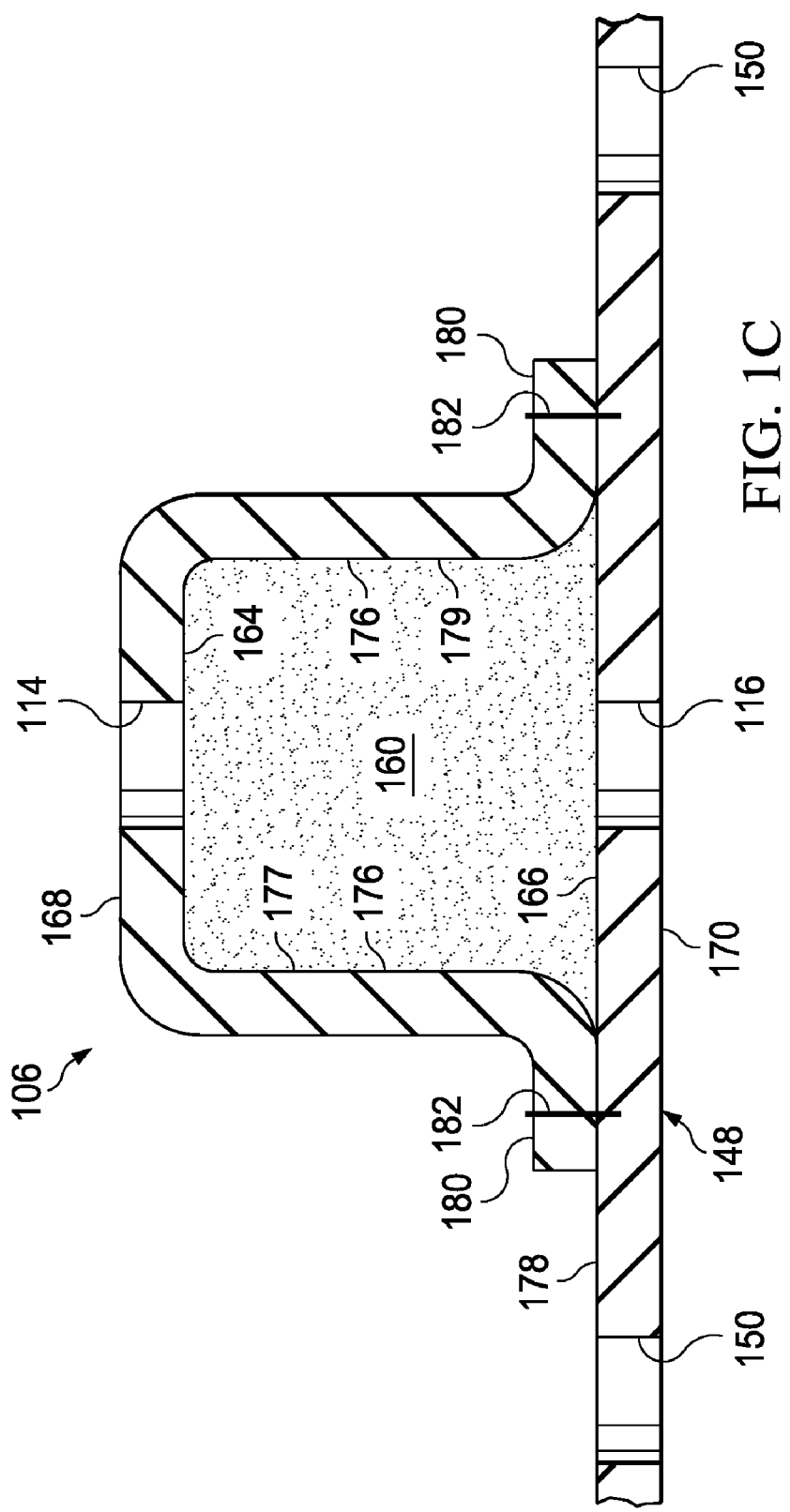
FIG. 1C is a lateral, cross-sectional view of an encapsulated leg member taken along line 1C-1C in FIG. 1A.
Figure 1D:
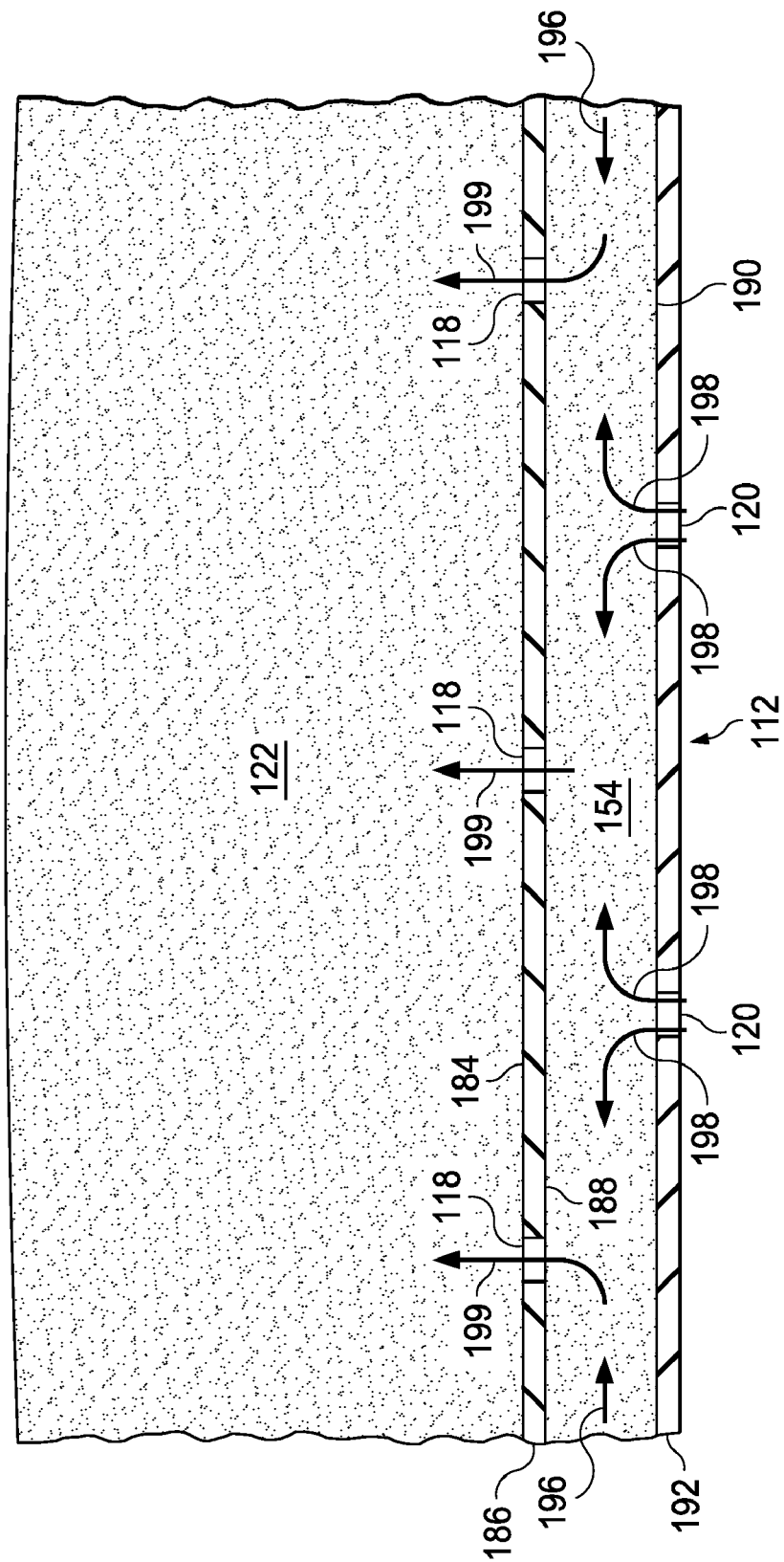
FIG. 1D is a cross sectional view of a portion of the system for controlling systemic inflammatory response in a patient's abdominal cavity of FIGS. 1A.
Figure 2:
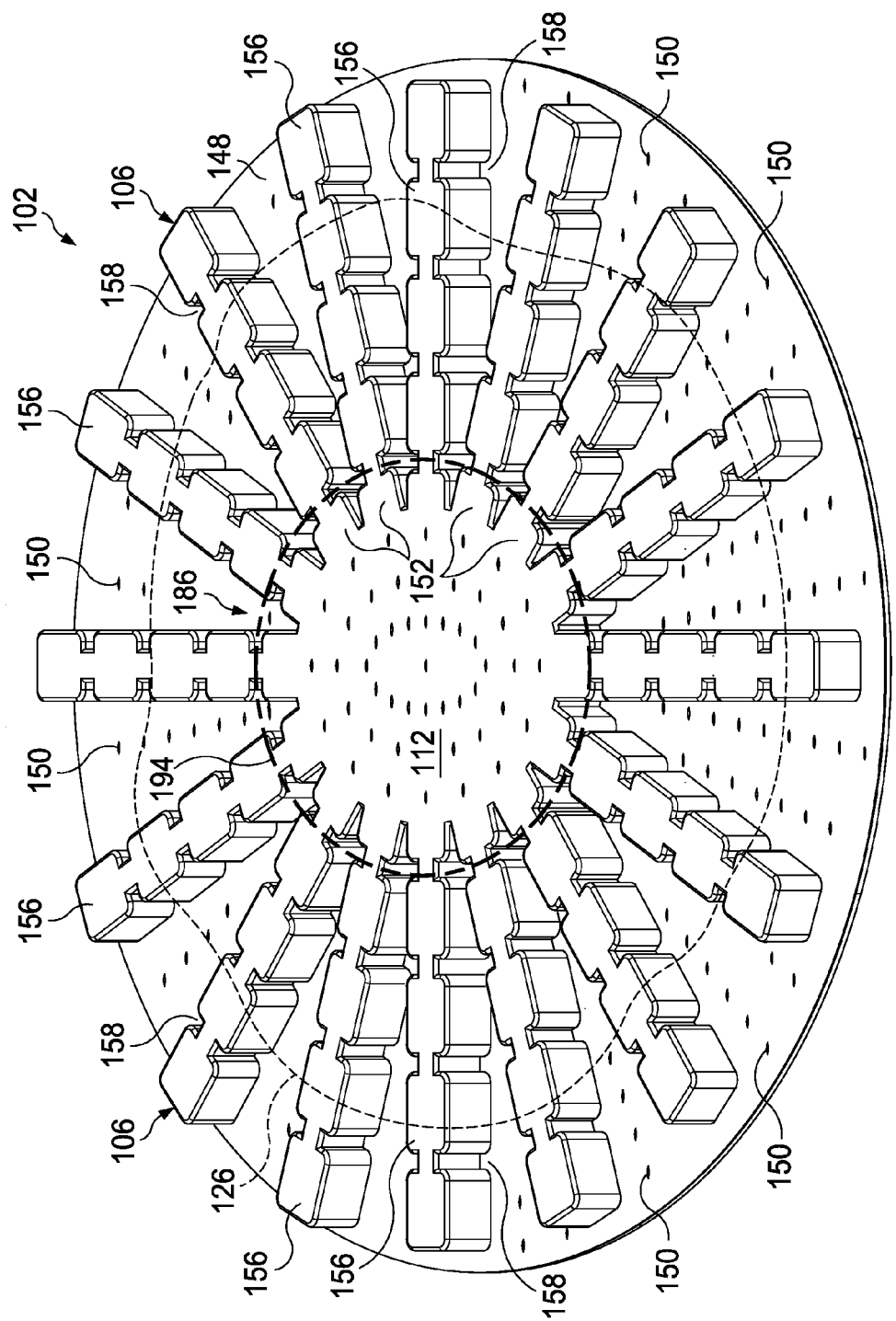
FIG. 2 is a schematic, perspective view of a portion of the system for controlling systemic inflammatory response in a patient's abdominal cavity of FIG. 1A.

Referring now to FIG. 1D and FIG. 2, the treatment device 102 includes a non-adherent drape 148. The non-adherent drape 148 may be formed of any non-adherent film material that helps prevent tissue from adhering to the non-adherent drape 148. In one embodiment, the non-adherent drape 148 is formed from a breathable polyurethane film. The non-adherent drape 148 is formed with a plurality of fenestrations 150. The plurality of fenestrations 150 may take any shape, such as circular openings, rectangular openings, polygon-shaped openings, etc., but are shown in FIG. 2 as slits, or linear cuts.

The treatment device 102 includes the central connection member 112 to which the plurality of encapsulated leg members 106 are coupled. The central connection member 112 is encapsulated by a first connection encapsulation member 186 and a second connection encapsulation member 192, except at leg coupling areas 152, which allow fluid communication between the central connection member 112 and the plurality of encapsulated leg members 106. The central connection member 112 has fenestrations 118 that allow fluid communication between a connection manifold member 154 and the manifold 122. Each of the plurality of encapsulated leg members 106 may be formed with or without a plurality of defined leg modules, such as leg modules 156. The adjacent leg modules 156 are fluidly coupled to each other and have a manipulation zone 158 between them.

Referring again to FIGS. 1A-1D, each of the plurality of encapsulated leg members 106 has a leg manifold member 160, which may be a single manifold member that runs between the leg modules 156 or may be discrete components of a manifold material that make up the leg manifold member 160. The leg manifold member 160 is disposed within an interior portion 162 of each of the encapsulated leg members 106. Each leg manifold member 160 has a first side 164 and a second, tissue-facing side 166. A first leg encapsulating member 168, which is formed with fenestrations 114, is disposed on the first side 164 of the leg manifold member 160. Similarly, a second leg encapsulating member 170, which has fenestrations 116, is disposed on the second, tissue-facing side 166 of the leg manifold member 160. The second leg encapsulating member 170 may be a portion of the non-adherent drape 148. As shown in the longitudinal cross section of FIG. 1B by arrows 172, fluid flows between the adjacent leg modules 156 towards the central connection member 112. As shown by arrows 174, the fluid is able to enter fenestrations 114 and 116 and flow into the leg manifold member 160 and then flow toward the central connection member 112 as represented by arrows 172.

Referring to FIG. 1C, a lateral cross section of a portion of the encapsulated leg member 106 is presented. As before, it can be seen that the first side 164 of the leg manifold member 160 is covered with the first leg encapsulating member 168, and that the second, tissue-facing side 166 of the leg manifold member 160 is covered by the second leg encapsulating member 170, which in this instance is a portion of the non-adherent drape 148. Thus, in this illustrative embodiment, the fenestrations 116 may be some of the plurality of fenestrations 150 in the non-adherent drape 148. In this illustrative embodiment, peripheral edges 176 of the leg manifold member 160 are also covered by a portion of the first leg encapsulating member 168. The peripheral edges 176 include a first lateral edge 177 and a second lateral edge 179. The first leg encapsulating member 168 covers the first side 164 and the peripheral edges 176 and extends onto a first surface 178 of the non-adherent drape 148 and forms extensions 180. The extensions 180 have been coupled to the second leg encapsulating member 170 by welds 182. The first leg encapsulating member 168 may, however, be coupled to the second leg encapsulating member 170 using any known technique, including welding (e.g., ultrasonic or RF welding), bonding, adhesives, cements, etc.

Referring again to FIG. 1D and FIG. 2, the central connection member 112 includes the connection manifold member 154 that is encapsulated within the first connection encapsulation member 186, which has fenestrations 118. The first connection encapsulation member 186 is disposed on a first side 188 of the connection manifold member 154. The second connection encapsulation member 192 is disposed on a second, tissue-facing side 190 of the connection manifold member 154. The second connection encapsulation member 192 is formed with fenestrations 120. The first connection encapsulation member 186 has a peripheral zone or edge 194 as shown in FIG. 2. In a similar fashion, the second connection encapsulation member 192 has a peripheral zone or edge (not explicitly shown) that lines up with the peripheral edge 194. The peripheral edge 194 of the first connection encapsulation member 186 is coupled to peripheral edge of the second connection encapsulation member 192, except at the leg coupling areas 152 in order to allow fluid within the plurality of encapsulated leg members 106 to flow into the connection manifold member 154 as suggested by arrows 196 in FIG. 1D. Fluid may also enter directly into the connection manifold member 154 by flowing through fenestrations 120 as suggested by arrows 198. The manifold 122 is disposed proximate to the first connection encapsulation member 186, and when reduced pressure is applied to the manifold 122, reduced pressure causes fluid to flow from the connection manifold member 154 through fenestrations 118 and into the manifold 122 as suggested by arrows 199. The fluid continues to flow in the direction of the reduced-pressure interface 128 through which the fluid is removed to the reduced-pressure delivery conduit 130.

Referring to FIGS. 1A-1D and 2, in operation, the illustrative system 100 may be used by first sizing the treatment device 102 by cutting to size. The non-adherent drape 148 with the plurality of encapsulated leg members 106 is disposed within the abdominal cavity through the body-cavity opening 126 and is distributed against the abdominal contents; this may include placing at least one encapsulated leg member 106 in or proximate the first paracolic gutter 108 or the second paracolic gutter 110. Once the treatment device 102 has been distributed, the manifold 122 is placed adjacent a first side 184 of the first connection encapsulation member 186. The sealing member 124 may then be applied over the body-cavity opening 126 to provide a pneumatic seal over the body-cavity opening 126, e.g., abdominal cavity 103.

In addition to the sealing member 124, the body-cavity opening 126 may be further closed or reinforced using mechanical closing means, e.g., staples, or using a reduced-pressure closure system. The sealing member 124 may be applied in a number of ways, but according to one illustrative embodiment, the releasable backing member that is on the adhesive layer 136 of the sealing member 124 is removed and then the sealing member 124 is placed against the patient's epidermis 134 about the body-cavity opening 126. The reduced-pressure interface 128, such as connector 138, is then attached to the sealing member 124 such that reduced pressure can be delivered by the reduced-pressure interface 128, through the sealing member 124, and to the manifold 122. The reduced-pressure delivery conduit 130 is fluidly coupled to the reduced-pressure interface 128 and to the reduced-pressure port 144 on the external reduced-pressure source 132.

The external reduced-pressure source 132 is activated and thereby provides reduced pressure into the reduced-pressure delivery conduit 130, which delivers reduced pressure to the reduced-pressure interface 128 and into the manifold 122. The manifold 122 distributes reduced pressure and draws fluid through fenestrations 118 from the connection manifold member 154. The connection manifold member 154 draws fluid, including pro-inflammatory stimuli, from the abdominal cavity 103 through fenestrations 120 and pulls fluid from the plurality of encapsulated leg members 106 as suggested by arrows 196. Fluid from the abdominal cavity 103 flows into the plurality of encapsulated leg members 106 through fenestrations 114 on the first leg encapsulating member 168 and through fenestrations 116 on the second leg encapsulating member 170 and then flows through the plurality of encapsulated leg members 106 as suggested by arrows 172 towards the connection manifold member 154. The fluid then flows through the manifold 122, the reduced-pressure interface 128, and into the reduced-pressure delivery conduit 130.

Figure 3A:
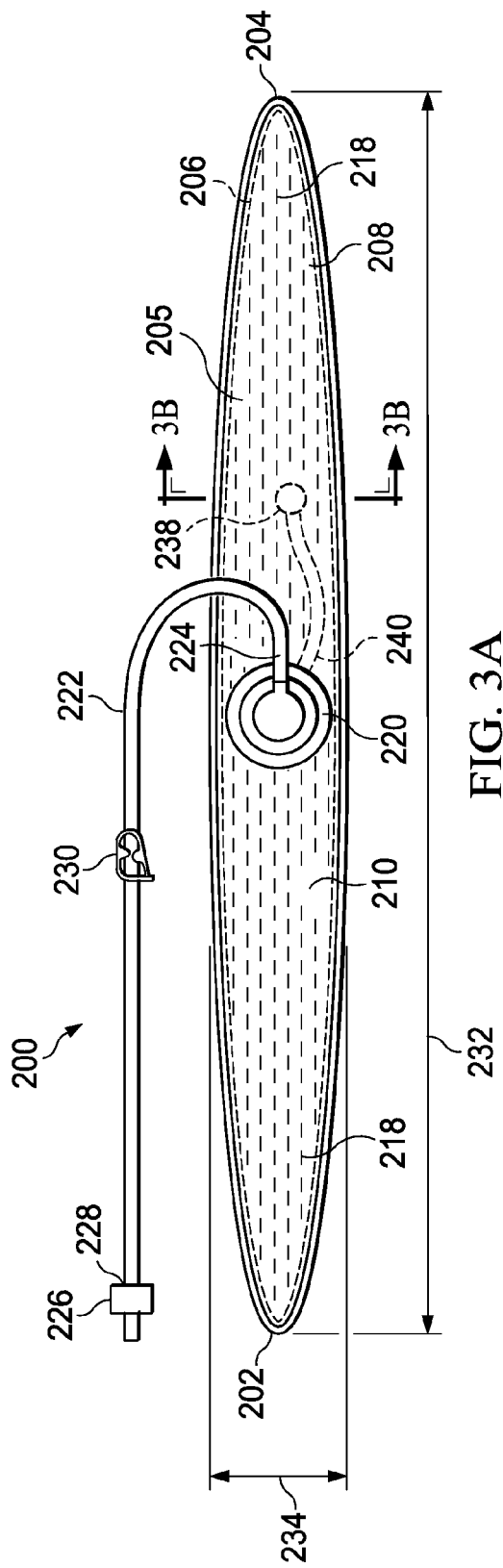
FIG. 3A is a schematic plan view of an illustrative embodiment of a reduced-pressure treatment device for use in system for controlling systemic inflammatory response.
Figure 3B:
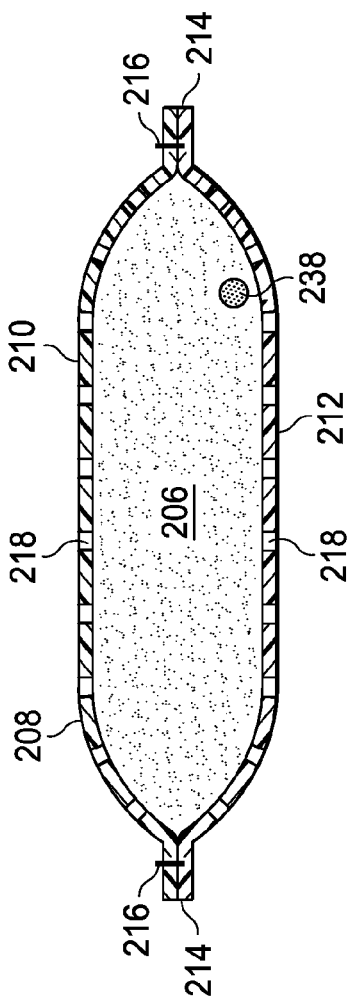
FIG. 3B is a schematic, cross-sectional view of the illustrative embodiment of a reduced-pressure treatment device of FIG. 3A taken along line 3B-3B.

Referring to FIGS. 3A and 3B, another illustrative embodiment of a treatment device 200 is presented. The treatment device 200 is a minimally-invasive treatment device in that the treatment device 200 is sized and configured to be introduced through a device incision, e.g., in the range of 0.3 centimeters to 4.0 centimeters in length. In some instances, the device incision may be larger e.g., 4.0 to 8.0 centimeters in length or more. The treatment device 200 may be formed as a one-piece design to facilitate placement and removal of the treatment device 200 from the abdominal cavity.

The treatment device 200 is formed as an encapsulated leg member 205 and has a first end 202 and a second end 204. The first end 202 and the second end 204 of the encapsulated leg member 205 are particularly well suited for placement in tight portions of the abdominal cavity, such as the paracolic gutters. The treatment device 200 is formed with a leg manifold member 206, which is enveloped in an encapsulating envelope 208. The leg manifold member 206 may be any manifold material, such as those referenced above for manifold 122 and leg manifold member 160. The leg manifold member 206 may have adequate stiffness to help facilitate placement of the encapsulated leg member 205.

The encapsulating envelope 208 may be formed by a first leg encapsulating member 210 and a second leg encapsulating member 212. Each leg encapsulating member 210, 212 has a peripheral edge 214. The peripheral edges 214 of the first leg encapsulating member 210 and the second leg encapsulating member 212 are coupled using any technique, including without limitation welding (e.g., ultrasonic or RF welding), bonding, adhesives, cements, etc. The peripheral edges 214 in this illustrative embodiment are shown coupled by a weld 216. The leg encapsulating members 210 and 212 may be formed from a fenestrated film or cover or any material referenced for the sealing member 124 above.

A plurality of fenestrations 218 are formed on the first leg encapsulating member 210 and the second leg encapsulating member 212, and thus fenestrations 218 are formed on the encapsulating envelope 208. A connecting interface 220, or reduced-pressure interface, is coupled to the encapsulating envelope 208 and is in fluid communication with the leg manifold member 206. A reduced-pressure delivery conduit 222 may be coupled to the connecting interface 220. The reduced-pressure delivery conduit 222 has a first end 224 and a second end 226. A fitting 228 may be placed on the second end 226 for a quick connection to an external reduced-pressure source (e.g., external reduced-pressure source 132 in FIG. 1A). The first end 224 of the reduced-pressure delivery conduit 222 is fluidly coupled to the connecting interface 220. A conduit clamp 230 may be placed on the reduced-pressure delivery conduit 222.

The encapsulated leg member 205 has a length (L) 232 and a width (W) 234. For the treatment device 200 shown in FIG. 3A, the aspect ratio (L/W) may, in an illustrative embodiment, range from 1.5 to 6.0. The aspect ratio of a shape is the ratio of the shape's longer dimension to its shorter dimension. It may be applied to two characteristic dimensions of a three-dimensional shape, such as the ratio of the longest and shortest axis, or for symmetrical objects that are described by just two measurements, such as the length and diameter of a rod. The aspect ratio of a torus is the ratio of the major axis R to the minor axis r. For a substantially flat leg member, such as treatment device 200 shown in FIG. 3A, the aspect ratio is the ratio L/W.

A pressure transducer 238 may be included within or alternatively attached to the treatment device 200. A transducer lead 240 may be coupled to the pressure transducer 238 and may run within or along the leg manifold member 206 to the connecting interface 220 and may run inside or along the reduced-pressure delivery conduit 222 to a point external to the patient where the transducer lead 240 may be coupled to equipment to provide an indication of the pressure within the abdominal cavity as experienced by the pressure transducer 238.

The use of treatment device 200 will now be described. The treatment device 200 may be deployed either through an open abdomen (see FIG. 1A) or percutaneously through a patient's epidermis (see epidermis 134 in FIG. 1A). The use of treatment device 200 is similar to other devices described herein. Whether through a device incision using a trocar or through an open abdomen application, the healthcare provider places the treatment device 200 within the abdominal cavity and preferably the first end 202 is placed on the abdominal contents and may be placed proximate a paracolic gutter and similarly the second end 204 is positioned on the abdominal contents and preferably at a paracolic gutter. The reduced-pressure delivery conduit 222 is run from within the abdominal cavity to a point external the abdominal cavity and is coupled to an external reduced-pressure source, e.g., external reduced-pressure source 132 in FIG. 1A. The device incision may be sealed (e.g., by a sealing member, such as the sealing member 124 in FIG. 1A). Reduced pressure is delivered via the reduced-pressure delivery conduit 222 to the connecting interface 220.

The connecting interface 220 is fluidly coupled to the leg manifold member 206 and delivers reduced pressure thereto. As such, fluids are pulled into the leg manifold member 206, delivered to the connecting interface 220, and delivered on to the reduced-pressure delivery conduit 222. The reduced-pressure delivery conduit 222 delivers the fluids to a location external the abdominal cavity for storage, disposal, or treatment. The removed fluids contain ascites, cytokines, and other fluids from the abdominal cavity that include pro-inflammatory stimuli. As the fluids are moved from the abdominal cavity, the inflammatory response is controlled.

The pressure transducer 238, which is associated with the treatment device 200, may be coupled using the transducer lead 240 to a device for determining the pressure within the abdominal cavity. The pressure within the abdominal cavity may be monitored to determine if additional treatment devices 200 should be deployed or if other intervention may be necessary. The removal of pro-inflammatory stimuli and reduced-pressure therapy within the abdominal cavity using treatment device 200 may continue for a period of time (T) ranging from 0.5 hours to more than 40 hours.

Once the healthcare provider decides that the need for treatment with the treatment device 200 has ended, the treatment device 200, which is a minimally-invasive treatment device, may be removed through the device incision. The treatment device 200 is removed through the device incision by administering a force on the reduced-pressure delivery conduit 222. Once the treatment device 200 is removed from the device incision, the device incision may be closed by any technique known, such as suture, bonding, bandage, staples, etc., or allowed to heal spontaneously. The use of treatment device 300 in FIG. 4 is analogous to the use of the treatment device 200, but provides for a greater area of treatment with a single device.

Figure 4:
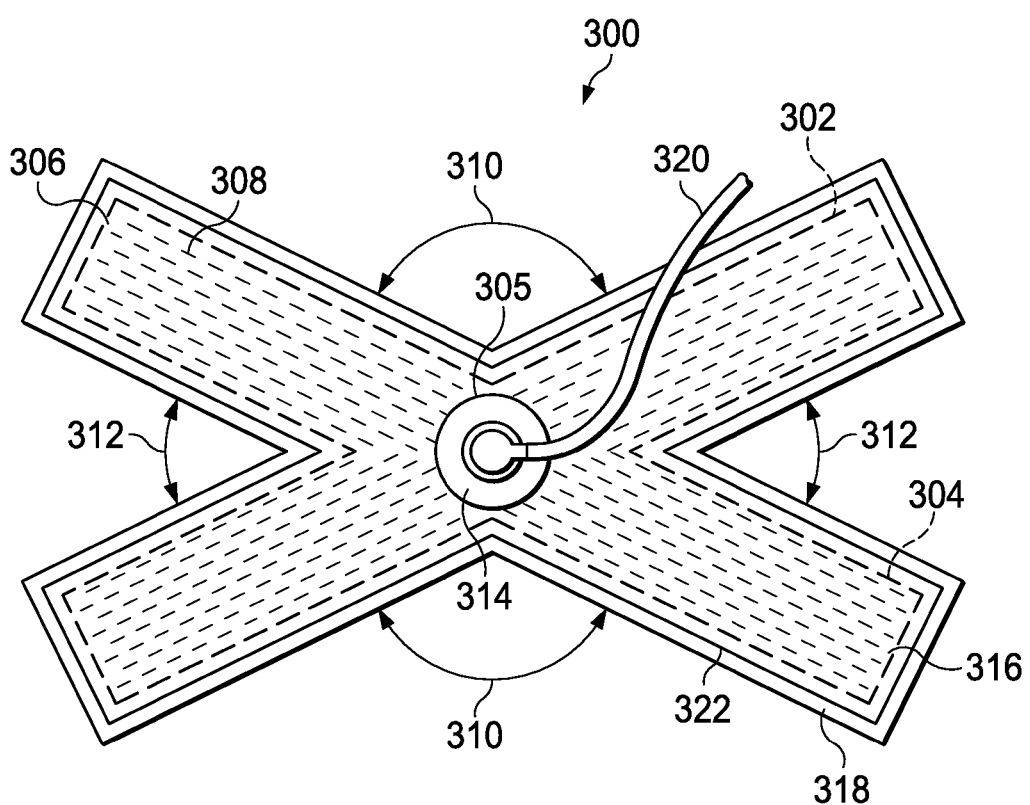
FIG. 4 is a schematic, plan view of an illustrative embodiment of a reduced-pressure treatment device.

Referring now to FIG. 4, another illustrative embodiment of a treatment device 300 is presented. The treatment device 300 is also a minimally-invasive treatment device in that the treatment device 300 may be deployed and removed through a device incision, e.g., in the range of 0.3 centimeters to 4.0 centimeters in length. The treatment device 300 is formed with a first leg manifold member 302 and a second leg manifold member 304. The first leg manifold member 302 and the second leg manifold member 304 intersect to form a central connection site 305. The first leg manifold member 302 and the second leg manifold member 304 may be formed from an integral piece of manifold member material (see, e.g., manifold materials mentioned in connection with manifold 122 above) or two pieces of manifold material may be coupled by any technique, e.g., glue. Again, the treatment device 300 may be of a one-piece design to facilitate its deployment and removal.

The first and second leg manifold members 302 and 304 may be encapsulated in an encapsulating envelope 306, which may be formed with fenestrations 308. The encapsulating envelope 306 may be formed with a film or covering, such as the material mentioned in connection with the sealing member 124 in FIG. 1A. The first leg manifold member 302 and second leg manifold member 304 may intersect to form angles, which may take any of a variety of sizes. The treatment device 300 may, in other words, form an "X" shape. In the embodiment shown, the angles include two obtuse angles 310 and two acute angles 312. The ends of the first leg manifold member 302 and second leg manifold member 304 within encapsulating envelope 306 facilitate fluid collection in multiple locations within the abdominal cavity.

A connecting interface 314 may be coupled to the central connection site 305 and is fluidly coupled to the first leg manifold member 302 and the second leg manifold member 304. The coupling of the connecting interface 314 to the central connection site 305 and a reduced-pressure delivery conduit 320 to the connecting interface 314 allows the treatment device 300 to be removed through a device incision, e.g., in the range of 0.3 centimeters to 4.0 centimeters in length, by providing a force initially on the reduced-pressure delivery conduit 320.

The encapsulating envelope 306 may be formed with a first encapsulating member 316 and a second encapsulating member (opposite side of the first and second leg manifold members 302, 304). The first encapsulating member 316 and second encapsulating member form an exterior layer that surrounds and covers the first leg manifold member 302 and the second leg manifold member 304. The first encapsulating member 316 and the second encapsulating member may be coupled at a peripheral portion 318, or peripheral edge, using any known technique, such as those previously mentioned. In the embodiment shown, an RF weld 322 is used to couple the peripheral portion 318 of the first encapsulating member 316 and the second encapsulating member. A reduced-pressure delivery conduit 320 may be fluidly coupled to the connecting interface 314 and to an external, reduced-pressure source (e.g., external reduced-pressure source 132 in FIG. 1A).

Referring to FIGS. 5A and 5B, another illustrative embodiment of a treatment device 400 is presented. The treatment device 400 includes a plurality of encapsulated leg members 402. Each encapsulated leg member 402 has a first end 404 and a second end 406. Each encapsulated leg member 402 may be placed at different locations within the abdominal cavity, such as in or near a paracolic gutter, behind the liver, etc. Each encapsulated leg member 402 has an exterior layer 408 formed with fenestrations 410. The exterior layer 408 forms an encapsulating envelope 412 that defines an interior space 414, which includes a leg manifold member 416. The exterior layer 408 may be formed from a film or covering, such as those mentioned in connection with the sealing member 124.

On the first end 404 of each encapsulated leg member 402 is a connecting interface 418. A plurality of connecting conduits 420 are coupled to the connecting interfaces 418 in a one-to-one fashion. Each connecting conduit 420 has a first end 422 and a second end 424. The second end 424 of the connecting conduit 420 is coupled to the connecting interface 418 of an associated encapsulated leg member 402. The first end 422 of the first connecting conduit 420 is coupled to an interface conduit 426. The interface conduit 426 has a first end 428 and a second end 430. The second end 430 of each interface conduit 426 couples to the first end 422 of one of the connecting conduits 420. A connector 438 may be used to couple the first end 422 of each of the connecting conduits 420 to the second end 430 of the interface conduit 426. The first end 428 of the interface conduit 426 may be coupled to a reduced-pressure delivery conduit (not shown) or directly to an external reduced-pressure source. In the embodiment shown in FIG. 5A, the plurality of encapsulated leg members 402 includes a first encapsulated leg member 432 and a second encapsulated leg member 434. It should be understood that any number of additional encapsulated leg members might be added as is appropriate for a particular need.

The use of the treatment device 400 will now be described. The treatment device 400 may be installed through an open abdomen or percutaneously using a trocar. The surgeon may make a device incision and insert a single encapsulated leg member 402, such as the first encapsulated leg member 432 along with its connecting conduit 420, into the patient's abdominal cavity. The surgeon may make other device incisions and insert other encapsulated leg members 402 with their associated connecting conduits 420 as deemed appropriate.

When a desired number of encapsulated leg members 402 has been placed within the abdominal cavity with their connecting conduits 420 extending through the device incisions, the first ends 422 of the connecting conduits 420 may be coupled to a connector 438. The connector 438 is connected to the interface conduit 426. The interface conduit 426 may be coupled to an external reduced-pressure source, e.g., external reduced-pressure source 132 in FIG. 1A. The treatment using one or more treatment devices 400 may then begin.

The treatment using the treatment device 400 may be carried out for a desired period of time (T). When treatment is terminated and removal of the treatment device 400 is desired, the connector 438 is removed so that a plurality of connecting conduits 420 remains initially extending from the patient. Each connecting conduit 420 may then be pulled to remove the associated encapsulated leg member 402 from its corresponding device incision. It should be recognized that with the treatment device 400, any number of encapsulated leg members 402 may be used without requiring an open abdomen for installation or removal.

With respect to the illustrative systems and devices that may be deployed using minimally invasive techniques on the context of an abdominal cavity, intervention may occur sooner as compared to a laparotomy. This may occur in practice because surgeons may be more likely to implement use of a minimally-invasive treatment device at a much earlier stage of management than a laparotomy since use of the minimally-invasive treatment device does not involve an incision of 30 centimeters or longer as is the case with many laparotomies. By offering the surgeon the opportunity to intervene with one or more minimally-invasive devices at an earlier stage post-injury, the time in which the abdominal viscera are exposed to the progressively harmful effects of allowing the inflammatory stimuli to persist until decompression could be substantially decreased and thus reducing in effect the severity and extent of disease.

Although the illustrative embodiments and methods advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A method for controlling systemic inflammatory response in a patient, the method comprising the steps of:

deploying a reduced-pressure treatment device proximate an internal tissue site;

wherein the internal tissue site is in an abdominal cavity interior to the patient's peritoneum;

fluidly coupling an external reduced-pressure source to the reduced-pressure treatment device to provide reduced pressure proximate the internal tissue site;

providing reduced pressure from the external reduced-pressure source to the reduced-pressure treatment device;

treating a pro-inflammatory milieu at the internal tissue site to control systemic inflammatory response throughout the patient's body; and wherein the step of treating a pro-inflammatory milieu comprises removing pro-inflammatory stimuli proximate the internal tissue site.

2. The method for controlling systemic inflammatory response of claim 1, wherein the reduced-pressure treatment device comprises a minimally-invasive treatment device;

wherein the step of fluidly coupling an external reduced-pressure source to the reduced-pressure treatment device comprises fluidly coupling a reduced-pressure delivery conduit to the minimally-invasive treatment device and to the external reduced-pressure source; and further comprising the step of removing the minimally-invasive treatment device from the abdominal cavity through a device incision.

3. The method for controlling systemic inflammatory response of claim 1, further comprising the step of determining an intra-abdomen pressure using a pressure transducer associated with the reduced-pressure treatment device.

4. The method for controlling systemic inflammatory response of claim 1, wherein the step of deploying a reduced-pressure treatment device comprises deploying the reduced-pressure treatment device at least partially into a paracolic gutter of the patient.

5. The method for controlling systemic inflammatory response of claim 1, wherein the step of providing reduced pressure from the external reduced-pressure source to the reduced-pressure treatment device comprises providing reduced pressure for at least a time (t) >0.5 hours.

6. The method for controlling systemic inflammatory response of claim 1, wherein the step of providing reduced pressure from the external reduced-pressure source to the reduced-pressure treatment device comprises providing reduced pressure for at least a time (t) >2.0 hours.

7. The method for controlling systemic inflammatory response of claim 1, wherein the step of providing reduced pressure from the external reduced-pressure source to the reduced-pressure treatment device comprises providing reduced pressure for at least a time (t) >20.0 hours.

8. The method for controlling systemic inflammatory response of claim 1, wherein the reduced-pressure treatment device comprises:

a plurality of encapsulated leg members, each encapsulated leg member having an interior portion with a leg manifold member and formed with fenestrations operable to allow fluid flow into the interior portion; and a central connection member, wherein the central connection member has a connection manifold member and wherein each leg manifold member is in fluid communication with the connection manifold member, the central connection member having a first side and a second, tissue-facing side.

9. The method for controlling systemic inflammatory response of claim 8, further comprising a connecting interface coupled to the central connection member.

10. The method for controlling systemic inflammatory response of claim 8, wherein each encapsulated leg member of the plurality of encapsulated leg members comprises:
   a first leg encapsulating member;
   a second leg encapsulating member formed with fenestrations;
   wherein the leg manifold member has a first side, a second, tissue-facing side, a first lateral edge, and a second lateral edge; and
   wherein the first leg encapsulating member is disposed proximate the first side of the leg manifold member, the second leg encapsulating member is disposed proximate the second, tissue-facing side of the leg manifold member, and the first leg encapsulating member and the second leg encapsulating member are coupled proximate the first lateral edge and the second lateral edge of the leg manifold member.

11. The method for controlling systemic inflammatory response of claim 1, wherein the reduced-pressure treatment device comprises:
   an encapsulated leg member, the encapsulated leg member having a leg manifold member, an encapsulating envelope formed with fenestrations and enveloping the leg manifold member, and wherein the encapsulated leg member has an aspect ratio greater than 3.0; and
   a connecting interface coupled to the encapsulated leg member and fluidly coupled to the leg manifold member.

12. The method for controlling systemic inflammatory response of claim 1, wherein the reduced-pressure treatment device comprises:
   an encapsulated leg member, the encapsulated leg member having a leg manifold member, an encapsulating envelope formed with fenestrations and enveloping the leg manifold member, and wherein the encapsulated leg member has an aspect ratio greater than 4.0; and
   a connecting interface coupled to the encapsulated leg member and fluidly coupled to the leg manifold member.

13. The method for controlling systemic inflammatory response of claim 1, wherein the reduced-pressure treatment device comprises:
   an encapsulated leg member, the encapsulated leg member having a leg manifold member, an encapsulating envelope formed with fenestrations and enveloping the leg manifold member, and wherein the encapsulated leg member has an aspect ratio greater than 5.0; and
   a connecting interface coupled to the encapsulated leg member and fluidly coupled to the leg manifold member.

14. The method for controlling systemic inflammatory response of claim 1, wherein the reduced-pressure treatment device comprises:
   a first leg manifold member;
   a second leg manifold member, wherein the first leg manifold member and the second leg manifold member intersect to from a central connection site;
   an encapsulating envelope forming an exterior layer over the first leg manifold member, the second leg manifold member, and the central connection site, and wherein the encapsulating envelope is formed with fenestrations to allow fluid flow into an interior portion.

15. The method for controlling systemic inflammatory response of claim 14, wherein the first leg manifold member and the second leg manifold member form two obtuse angles and two acute angles.

16. The method for controlling systemic inflammatory response of claim 1, wherein the reduced-pressure treatment device comprises:
   a plurality of encapsulated leg members, each having an interior portion with a leg manifold member and formed with fenestrations operable to allow fluid flow into the interior portion, and each having a first end and a second end;
   wherein each of the plurality of encapsulated leg members has a connecting interface on the first end;
   a plurality of connecting conduits, each having a first end and a second end;
   an interface conduit having a first end and second end;
   wherein the first end of each of the plurality of connecting conduits is coupled to the second end of the interface conduit; and
   wherein the second end of each of the plurality of connecting conduits is coupled to the plurality of encapsulated leg members at the connecting interface.

* * * * *